US011402381B2

(12) United States Patent
Krause et al.

(10) Patent No.: US 11,402,381 B2
(45) Date of Patent: Aug. 2, 2022

(54) METHODS OF IDENTIFYING AN INDIVIDUAL TO BE TREATED BY CHEMOTHERAPY BASED ON CYTOKERATIN-19 FRAGMENTS (CYFRA 21-1) AND CARCINOEMBRYONIC ANTIGEN (CEA) MARKER MOLECULES AND RELATED USES (71) Applicant: Roche Diagnostics Operations, Inc., Indianapolis, IN (US)

(72) Inventors: Friedemann Krause, Penzberg (DE); Vinzent Rolny, Munich (DE); Farshid Dayyani, Irvine, CA (US); Achim Escherich, Hergiswil (CH); Birgit Wehnl, Munich (DE); Ying He, Munich (DE); Julia Riedlinger, Ottobrunn (DE); Felix Herth, Heidelberg (DE); Thomas Muley, Heidelberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 62 days.

(21) Appl. No.: 15/952,731

(22) Filed: Apr. 13, 2018

(65) Prior Publication Data
US 2018/0231557 A1   Aug. 16, 2018

Related U.S. Application Data (63) Continuation of application No. PCT/EP2016/075313, filed on Oct. 21, 2016.

(30) Foreign Application Priority Data

Oct. 23, 2015 (EP) .................................. 15003039

(51) Int. Cl.
*G01N 33/50* (2006.01)
*G01N 33/574* (2006.01)

(52) U.S. Cl.
CPC .  *G01N 33/57423* (2013.01); *G01N 33/57484* (2013.01); *G01N 2333/4742* (2013.01); *G01N 2333/70596* (2013.01)

(58) Field of Classification Search
CPC ................................................ G01N 33/57484
USPC ........................................................ 435/7.23
See application file for complete search history.

(56) References Cited

U.S. PATENT DOCUMENTS

| | | | |
|---|---|---|---|
| 5,283,173 A | 2/1994 | Fields et al. | |
| 5,468,614 A | 11/1995 | Fields et al. | |
| 2005/0244973 A1* | 11/2005 | Andel, III | G01N 33/57434 436/64 |
| 2006/0155200 A1* | 7/2006 | Ng | A61B 5/0472 600/509 |
| 2010/0179067 A1* | 7/2010 | Patz, Jr. | G01N 33/57423 506/8 |
| 2012/0076725 A1* | 3/2012 | Birse | A61P 11/00 424/1.49 |
| 2015/0038365 A1 | 2/2015 | Aghvanyan et al. | |

FOREIGN PATENT DOCUMENTS

| | | |
|---|---|---|
| EP | 2071337 A1 | 6/2009 |
| EP | 2908133 A1 | 8/2015 |
| JP | 5221825 B1 | 3/2013 |
| WO | 2011/140234 A1 | 11/2011 |
| WO | 2012/160177 A1 | 11/2012 |

OTHER PUBLICATIONS

Mantovani (European Journal of Cancer, vol. 30A, No. 3, p. 363-369, 1994) (Year: 1994).*
Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Hanagiri et al (Lung Cancer, 2011, 74: 112-117).*
Song et al (Chin Med, 2011, 124(20): 3244-3248).*
Okamura et al (Lung Cancer, 2013, 80: 45-49).*
Edge, Stephen B et al., Editors, Cancer Staging Manual, American Joint Committee on Cancer, 2010, pp. 253-270, 7th Edition, Chapter 25.
Kaplan, E. L. and Meier, Paul, Nonparametric Estimation From Incomplete Observations, American Statistical Association Journal, 1958, pp. 457-481.
Morgensztern, Daniel et al., Adjuvant chemotherapy for patients with T2N0M0 non-small cell lung cancer, Journal of Clinical Oncology, 2015, Abstract 7520, vol. 33, No. 15 Supp.
Blankenberg, Florian et al., Preoperative CYFRA21-1 and CEA as Prognostic Factors in Patients with Stage I Non-Small Cell Lung Cancer, Tumor Biology, 2008, pp. 272-277, vol. 29.
Bodenmüller, H. et al., Lung cancer-associated keratin 19 fragments: development and biochemical characterisation of the new serum assay Enzymun-Test® CYRFA 21-1, The International Journal of Biological Markers, 1994, pp. 75-81, vol. 9, No. 2.
Ebert, W., et al., Cytokeratin 19 Fragment CYFRA 21-1 Compared with Carcinoembryonic Antigen, Squamous Cell Carcinoma Antigen and Neuron-Specific Enolase in Lung Cancer Results of an International Multicentre Study, European Journal of Clinical Chemistry and Clinical Biochemistry, 1994, pp. 189-199, vol. 32, No. 3.
Hanagiri, Takeshi et al., Preoperative CYFRA 21-1 and CEA as prognostic factors in patients with stage I non-small cell lung cancer, Lung Cancer, 2011, pp. 112-117, vol. 74.
International Search Report dated Nov. 22, 2016, in Application No. PCT/EP2016/075313, 6 page.
Kozu, Yoshiki et al., Prognostic significance of postoperative serum carcinoembryonic antigen levels in patients with completely resected pathological-stage I non-small cell lung cancer, Journal of Cardiothoracic Surgery, 2013, 7 pp., vol. 8, No. 106.

(Continued)

Primary Examiner — Sean E Aeder
(74) Attorney, Agent, or Firm — Stinson LLP (57) ABSTRACT The present disclosure relates to a method of identifying an individual having non-small cell lung carcinoma as to be treated by chemotherapy based on marker molecules cytokeratin-19 fragments (CYFRA 21-1) and carcinoembryonic antigen (CEA) as well as the use of the marker molecules for the identification of an individual to be treated by chemotherapy.

8 Claims, 3 Drawing Sheets (56) References Cited

OTHER PUBLICATIONS

Kulpa, Jan et al., Carcinoembryonic Antigen, Squamous Cell Carcinoma Antigen, CYFRA 21-1, and Neuron-specific Enolase in Squamous Cell Long Cancer Patients, Clinical Chemistry, 2002, pp. 1931-1937, vol. 48, No. 11.
Moro, D. et al., CEA, CYFRA21-1 and SCC in non-small cell lung cancer, Lung Cancer, 1995, pp. 169-176, vol. 13.
Muley, T. et al., Tumor Marker Index (TMI) Based on CYFRA 21-1 and CEA Identifies P-Stage I NSCLC Patents with High Risk of Recurrence, Potential Candidates for Adjuvant Chemotherapy?, Tumor Biology, 2010, p. S87, vol. 31, Supplement 1.
Muley, Th. et al., Do Postoperatively Elevated CYFRA 21-1 or CEA Values Qualify for Adjuvant Chemotherapy in Completely Resected Stage I NSCLC Patients?, International Journal of Cancer Research, Abstracts of the 12th International Hamburg Symposium on Tumor Markers, Nov. 30-Dec. 2, 2013, 1 pg., vol. 23, No. 6B, Abstract 50.
Muley, Thomas et al., Increased CYFRA 21-1 and CEA Levels are Negative Predictors of Outcome in p-Stage I NSCLC, Anticancer Research, 2003, pp. 4085-4095, vol. 23.
Muley, Thomas et al., Tumor volume and tumor marker index based on CYFRA 21-1 and CEA are strong prognostic factors in operated early stage NSCLC, Lung Cancer, 2008, pp. 408-415, vol. 60.
Plebani, M. et al., Clinical evaluation of seven tumour markers in lung cancer diagnosis: can any combination improve the results?, British Journal of Cancer, 1995, pp. 170-173, vol. 72.
Rich, Jason T. et al., A practial guide to understanding Kaplan-Meier curves, Otolaryngology-Head and Neck Surgery, 2010, pp. 331-336, vol. 143.
Scouten, William H., A Survey of Enzyme Coupling Techniques, Methods in Enzymology, 1987, pp. 30-65, vol. 135, Chapter 2.
Sturgeon, Catharine, Practice Guidelines for Tumor Marker Use in the Clinic, Clinical Chemistry, 2002, pp. 1151-1159, vol. 48, No. 8.
Tijssen, P., Practice and Theory of Enzyme Immunoassays, 1990, pp. 43-78, 108-115, Elsevier.
Van Der Gaast, A. et al., Evaluation of a new tumour marker in patients with non-small-cell lung cancer: Cyfra 21.1, British Journal of Cancer, 1994, pp. 525-528, vol. 69.
Wieskopf, Brian et al., Cyfra 21-1 as a Biologic Marker of Non-small Cell Lung Cancer Evaluation of Sensitivity, Specificity, and Prognostic Role, Chest, 1995, pp. 163-169, vol. 108.

* cited by examiner

METHODS OF IDENTIFYING AN INDIVIDUAL TO BE TREATED BY CHEMOTHERAPY BASED ON CYTOKERATIN-19 FRAGMENTS (CYFRA 21-1) AND CARCINOEMBRYONIC ANTIGEN (CEA) MARKER MOLECULES AND RELATED USES

CROSS-REFERENCE TO RELATED APPLICATIONS

This application is a continuation of International Application No. PCT/EP2016/075313 filed Oct. 21, 2016, which claims priority to European Application No. 15003039.3 filed Oct. 23, 2015, both of which are hereby incorporated in their entirety.

BRIEF SUMMARY OF THE DISCLOSURE

The present invention relates to a method of identifying an individual having non-small cell lung carcinoma as to be treated by chemotherapy based on marker molecules cytokeratin-19 fragments (CYFRA 21-1) and carcinoembryonic antigen (CEA) as well as the use of the marker molecules for the identification of an individual to be treated by chemotherapy.

BACKGROUND OF THE DISCLOSURE

Lung cancer is the most common cancer worldwide, with about 1.8 million new cases and 1.6 million deaths in 2012. Treatment for lung cancer depends on the cancer's specific cell type, how far it has spread, and the person's performance status. Common treatments include palliative care, surgery, chemotherapy, and radiation therapy.

Targeted therapy of lung cancer is growing in importance for advanced lung cancer. After successful therapy, patients need to be carefully monitored for a relapse. Prognostic factors in non-small cell lung cancer (NSCLC) include presence or absence of pulmonary symptoms, tumor size, cell type (histology), degree of spread (stage) and metastases to multiple lymph nodes, and vascular invasion. At present the best prognosis for NSCLC is achieved with complete surgical resection of stage IA disease, with up to 70% five-year survival. However, some patients might further benefit from chemotherapy.

The accepted standard of care for patient prognosis and adjuvant chemotherapy decision in early stage NSCLC is tumor size. However, even some patients with small tumors might need adjuvant chemotherapy, whereas on the other hand patients with larger stage II tumors might be cured with surgery alone (Morgensztern D et al., 2015, J Clin Oncol 33 (suppl): Abstr 7520). Thus, using the clinical standard of care, some patients might be undertreated and others overtreated.

Accordingly, there is still a need for a suitable method for identifying an individual with lung carcinoma as to be treated by chemotherapy.

Surprisingly, it was found that a subgroup of lung carcinoma patients, namely those diagnosed with non-small cell lung carcinoma subtype squamous cell carcinoma (SCC-NSCLC) stage I or II, do highly benefit from chemotherapy, if the levels for markers cytokeratin-19 fragments (CYFRA 21-1) and carcinoembryonic antigen (CEA) are elevated (high risk group), whereas those not having elevated levels (low risk group) do not benefit from chemotherapy.

Currently, there is no blood biomarker based standard of care to decide whether patients with SCC-NSCLC with stage I or II should receive adjuvant chemotherapy (AC) to decrease their risk of relapse. Previous publications have suggested that the Tumor-Marker-Index (TMI) might define a high risk group in patients with all NSCLC who might benefit from AC (Muley T, 2010, Tumor Biology 31, Suppl. 1: S87). As shown in the present examples it is important to distinguish between different NSCLC histologic subtypes. The marker combination of Cyfra21-1 and CEA together with the stage information (stage I or II) establishes relapse-free survival (RFS) in SCC-NSCLC, but there is no additional benefit from chemotherapy in non small cell lung carcinoma subtype adenocarcinoma, i.e. the markers are not predictive for that subgroup. The innovative finding of the present invention is the focus of SCC histology, the addition of T stage and applicability to both stage I and II, all of which are different from the methods described above and based on the tumor marker index, only.

Figure 1A:
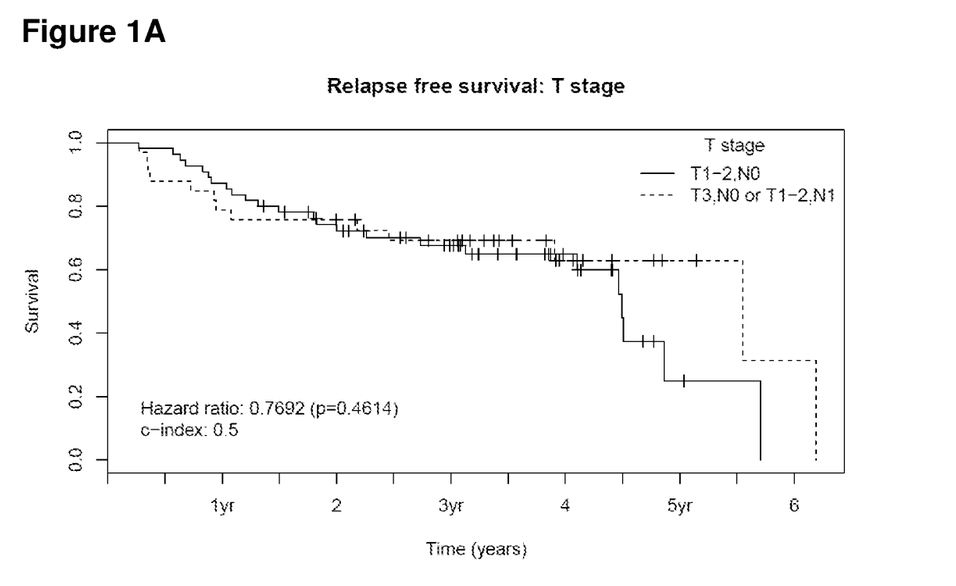
FIG. 1A and FIG. 1B illustrate relapse free survival of patients diagnosed with SCC-NSCLC stage I and II.
Figure 2A:
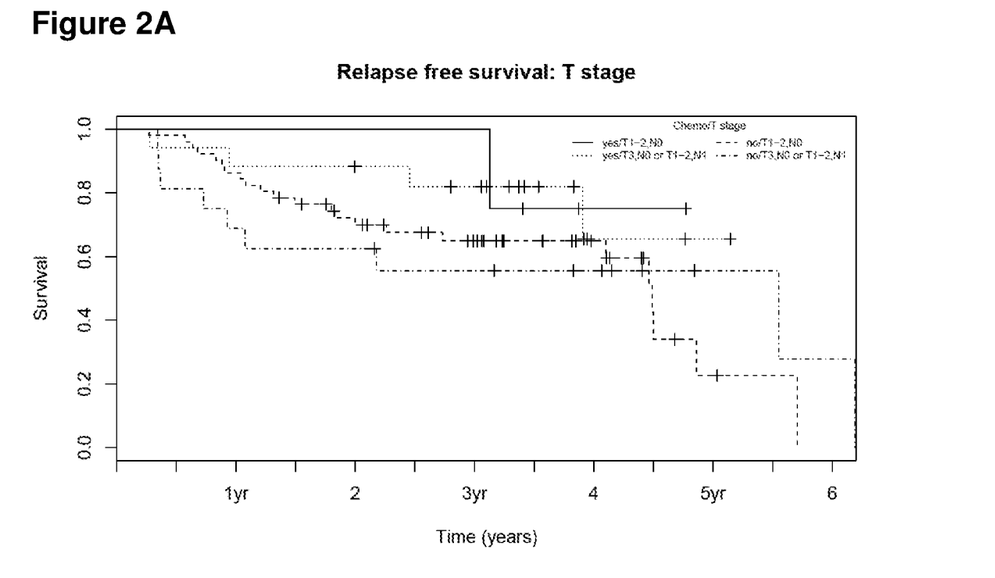
FIG. 2A and FIG. 2B illustrate a comparison of relapse free survival of subgroups of SCC-NSCLCpatients depending on the treatment with chemotherapy. The subgroups of patients as specified in FIGS. 1A (categorized according to accepted standard of care) and 1B (categorized based on Cyfra21-1 and CEA levels according to the present invention) were assessed for the effectiveness of adjuvant chemotherapy by determining time-dependent relapse free survival.
Figure 3A:
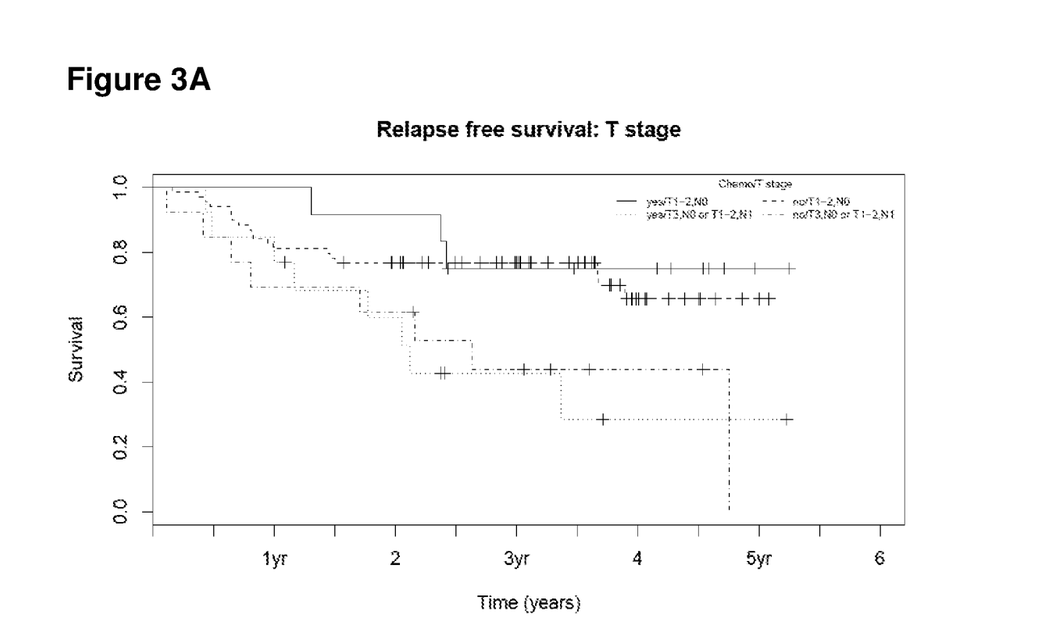
FIG. 3A and FIG. 3B illustrate a comparison of relapse free survival of subgroups of adeno-NSCLCpatients depending on the treatment with chemotherapy. The subgroups of patients as specified in FIGS. 1A (categorized according to accepted standard of care) and 1B (categorized based on Cyfra21-1 and CEA levels according to the present invention) were assessed for the effectiveness of adjuvant chemotherapy by determining time-dependent relapse free survival.

The inventors were able to show that the current standard of care, i.e. T stage alone, is not prognostic or predictive in SCC-NSCLC patients (see FIG. 1A) and in adenocarcinoma NSCLC patients (see FIG. 3A). As shown in FIG. 2A, tumor stage alone cannot distinguish different prognostic groups in SCC-NSCLC and T stage alone also cannot predict which group of patients should receive chemotherapy since in both groups (referred to as T1-2, N0 and T3, N0 or T1-2, N1) the RFS is only improved slightly with chemotherapy (see FIG. 2A). That means that the current clinical standard is not optimal for patient selection for chemotherapy in SCC-NSCLC.

Figure 1B:
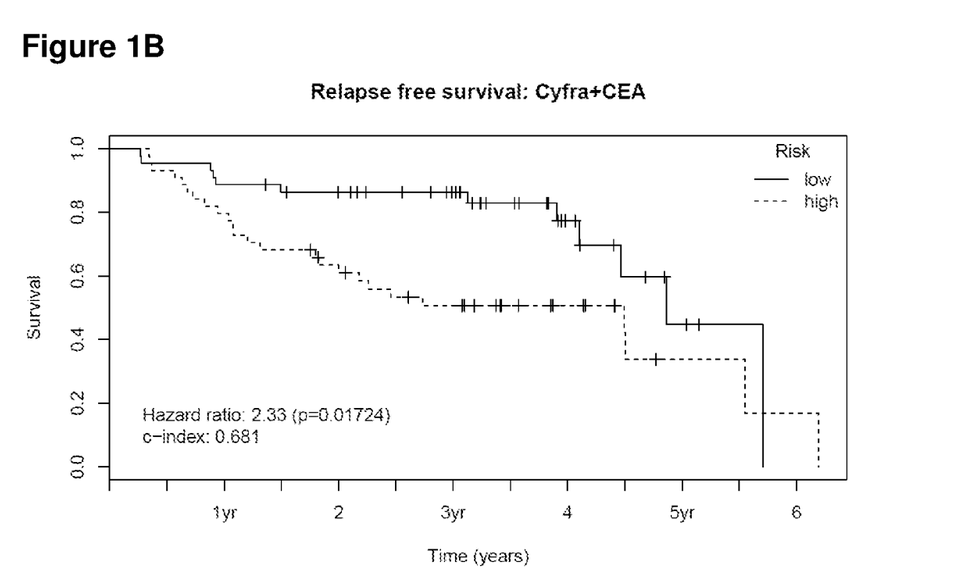
Figure 2B:
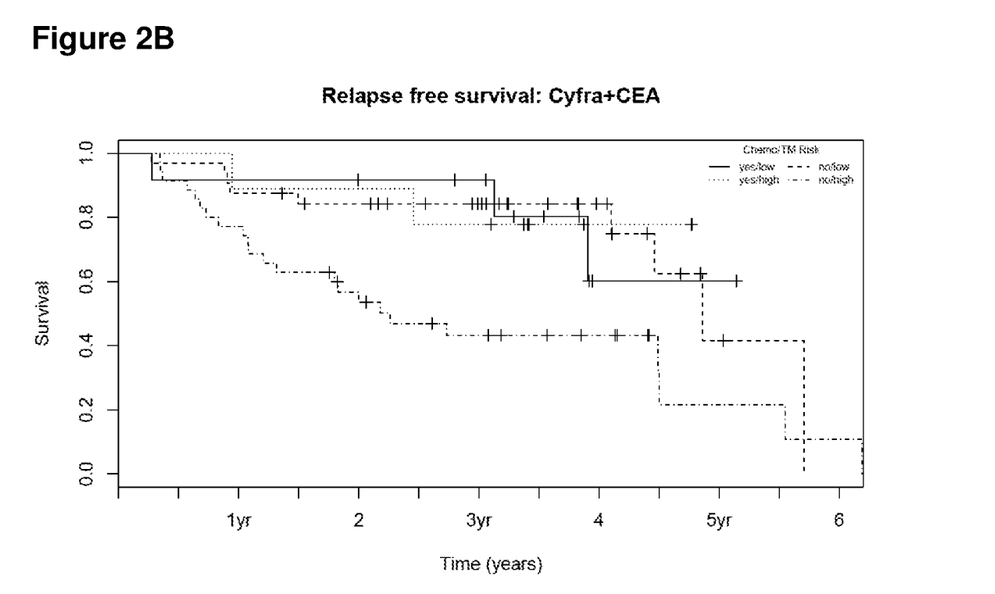

Based on the marker combination of the present disclosure (Cyfra21-1 and CEA), individuals diagnosed with (having) SCC-NSCLC stage I or II could be separated into two prognostic groups with different risks/probabilities for relapse or relapse-free survival (see FIG. 1B). As shown in FIG. 2B, the low risk group (fullline and dashed line, respectively) does not need chemotherapy after surgery, but the high risk group will clearly and significantly benefit from adjuvant chemotherapy (dotted line vs. dashed/dotted line). There is no significant difference between the fullline (low risk patient with chemotherapy) and dashed line (low risk patient without chemotherapy), i.e. adjuvant chemotherapy does not change the RFS in low risk patients, but there is a large difference between the dotted line (high risk patient with chemotherapy) and the dashed/dotted line (high risk patient without chemotherapy), showing a significant improvement in RFS with the addition of adjuvant chemotherapy in the high risk patients.

Figure 3B:
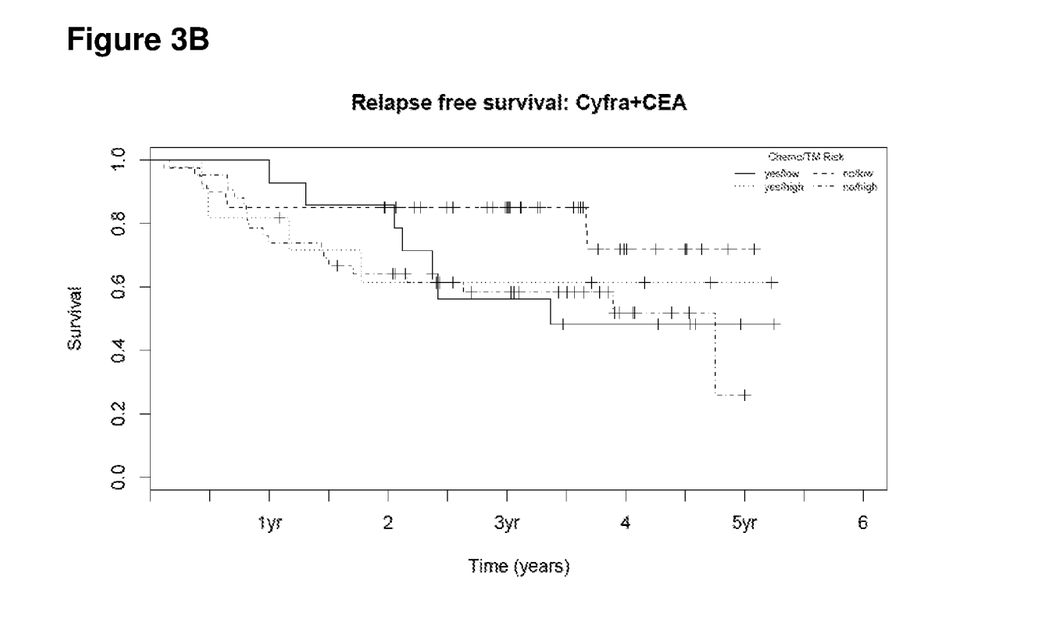

In contrast to the above group of individuals diagnosed with SCC-NSCLC stage I or II, individual diagnosed with non small cell lung carcinoma subtype adenocarcinoma do not show an additional benefit from chemotherapy in, i.e. the markers are not predictive for that subgroup. As shown in FIG. 3B, neither the low risk group (fullline and dashed line, respectively) nor the high risk group will significantly benefit from adjuvant chemotherapy (dotted line vs. dashed/dotted line). There is no significant difference between the fullline (low risk patient with chemotherapy) and dashed line (low risk patient without chemotherapy) and there is also no significant difference between the dotted line (high risk patient with chemotherapy) and the dashed/dotted line (high risk patient without chemotherapy), i.e. adjuvant chemotherapy does not change the RFS in either of the risk groups.

In summary, the important advantage in the present approach is the fact that it can identify the individuals who should (high risk group) and who should not (low risk group) receive chemotherapy after surgery for non-small cell lung carcinoma subtype squamous cell carcinoma (SCC-NSCLC).

FIGURES

FIG. 1A: In FIG. 1A, patients were subdivided in accordance with the present standard, i.e. patients classified as T1-2, N0 (chemotherapy not recommended; indicated by fullline) and T3, N0 or T1-2, N1 (to be treated by adjuvant chemotherapy; indicated by dashed line ). The lines indicate relapse free survival of the two subgroups depending on the time after surgery.

FIG. 1B: In FIG. 1B, patients were categorized based on the levels of the markers Cyfra21-1 and CEA in the patient's samples and relapse free survival was monitored in a time-dependent manner. Patients with elevated levels of the markers were found to have a high risk for relapse (indicated by dashed line ), whereas those with lower levels were found to have a low risk for relapse (indicated by fullline).

FIG. 2A: As shown in FIG. 2A, with the current standard of care, i.e. T stage alone, chemotherapy does not significantly improve relapse free survival.

FIG. 2B: As shown in FIG. 2B, in the low risk group (fullline and dashed line ) chemotherapy does not positively affect relapse free survival, but in the high risk group ( dotted line vs. dashed/dotted line ) relapse free survival is increased by chemotherapy, which proves that this subgroup of patients identified according to the present invention clearly and significantly benefits from adjuvant chemotherapy.

FIG. 3A: As shown in FIG. 3A, with the current standard of care, i.e. T stage alone, relapse free survival remains unchanged.

FIG. 3B: As shown in FIG. 3B, there is also no significant difference between the fullline (low risk patient with chemotherapy) and dashed line (low risk patient without chemotherapy) and there is also no significant difference between the dotted line (high risk patient with chemotherapy) and the dashed/dotted line (high risk patient without chemotherapy), i.e. adjuvant chemotherapy does not change the relapse free survival in either of the risk groups.

DETAILED DESCRIPTION OF THE DISCLOSURE

In a first aspect, the present invention relates to a method of identifying an individual having non-small cell lung carcinoma subtype squamous cell carcinoma (SCC-NSCLC) stage I or II as to be treated by chemotherapy, the method comprising
a) measuring in a sample obtained from the individual the amount or concentration of the marker molecules cytokeratin-19 fragments (CYFRA 21-1) and carcinoembryonic antigen (CEA),
b) obtaining a combined value by weighted calculation of the amount or concentration of the marker molecules measured in step (a); and
c) identifying the subject as to be treated by chemotherapy by comparing the combined value for the markers obtained in step (b) to the cut-off value of the combined values as established in a reference population, wherein a combined value above of the cut-off value indicates that the individual is to be treated by chemotherapy.

Lung cancer is also known as carcinoma of the lung or pulmonary carcinoma, and is a malignant lung tumor characterized by uncontrolled cell growth in tissues of the lung. If left untreated, this growth can spread beyond the lung by process of metastasis into nearby tissue or other parts of the body. Most cancers that start in the lung, known as primary lung cancers, are carcinomas that derive from epithelial cells. The main four histological types of lung cancer are squamous cell carcinoma, adenocarcinoma, large cell carcinoma and small cell carcinoma (SCLC). The first three subtypes are generally referred to as non-small-cell carcinoma (NSCLC) and account for approximately 80% of lung cancer. Diagnosis of the lung tumor is in general based on imaging methods and analysis of biopsy samples. The 2004 World Health Organization (WHO) schema of lung tumors has been the foundation for lung cancer classification. This incorporated a number of developments, including recognition of lung carcinoma heterogeneity, the introduction of diagnostic immunohistochemical staining (IHC) techniques for the routine diagnosis of some neuroendocrine tumors, and the recognition of newly described entities such as fetal adenocarcinoma, cystic mucinous tumors, and large cell neuroendocrine carcinoma.

In 2011, a multidisciplinary expert panel representing the International Association for the Study of Lung Cancer (IASLC), the American Thoracic Society (ATS), and the European Respiratory Society (ERS) proposed a major revision of the classification system. These changes primarily affect the classification of adenocarcinoma and its distinction from squamous cell carcinoma. The present international standard for classification of tumors by oncologists and pathologists is provided by the "WHO Classification of Tumours of the Lung, Pleura, Thymus and Heart" (Travis et al, 2015, WHO Classification of Tumours, Volume 7, fourth edition). In case of doubt in the context of the present invention, the above standard is to be applied.

Squamous cell lung carcinoma is a type of non-small cell lung cancer formed from reserve cells, i.e. round cells that replaced injured or damaged cells in the lining of the bronchi, the lung's major airways. Squamous cell tumors usually occur in the lung's central portions or in one of the main airway branches. These tumors can form cavities in the lung if they grow to a large size. Making up between 25 and 30 percent of all lung cancers, squamous cell carcinoma can spread to bones, adrenal glands, the liver, small intestine, or brain. The prognosis for an advanced stage of this type of lung cancer is poor. However, five-year survival rates can be as high as 35 to 40 percent for those who have localized lung cancer that is identified and removed in its early stages. These five-year survival rates approach 85 percent for patients under age 30. This type of cancer is almost always caused by smoking. Secondary risk factors include age, family history, and exposure to secondhand smoke, mineral and metal dust, asbestos, or radon.

Histologic diagnosis of squamous cell carcinoma is predicated upon the presence of keratin production by tumor cells and/or intercellular desmosomes (referred to as "intercellular bridges"). Some tumors that are either predominantly spindled (spindle cell variant of pleomorphic carcinoma) or have a characteristic pattern of peripheral palisading may also be classified as squamous cell carcinoma. Historically, most squamous cell carcinoma (60 to 80 percent) arose in the proximal portions of the tracheobronchial tree, through a squamous metaplasia, dysplasia, carcinoma in situ sequence (squamous carcinoma in situ). A minority of cases occur peripherally and may be associated with bronchiectatic cavities or scars. Central and peripheral squamous cell carcinomas may show extensive central necrosis with resulting cavitation. A small subset of central, well differentiated squamous cell carcinoma occur as exophytic, endobronchial, papillary lesions. Patients with this unusual variant of squamous cell carcinoma typically present with persistent cough, recurrent hemoptysis, or relapsing pulmonary infections due to airway obstruction.

Adenocarcinoma is the most common type of lung cancer in contemporary series, accounting for approximately one-half of lung cancer cases. It is a type of lung cancer that forms in mucus-secreting glands throughout the body. Adenocarcinoma is usually found in outer parts of the lung, tends to grow slower than other types of lung cancer, and is more likely to be found before it has spread outside of the lung. It occurs mainly in current or former smokers, but it is also the most common type of lung cancer seen in non-smokers. It is more common in women than in men, and it is more likely to occur in younger people than other types of lung cancer. The increased incidence of adenocarcinoma is thought to be due to the introduction of low-tar filter cigarettes in the 1960s, although such causality is unproven.

Presently, tumor staging for NSCLC is based on the "The Revised International System for Staging Lung Cancer". Lung cancer has been categorized considering the information from a clinical database of more than 5,000 patients, was adopted in 2010 by the American Joint Committee on Cancer (AJCC) and the Union Internationale Contre le Cancer.

The T (primary tumor) classification is as follows:
T1=tumor≤3 cm in size
T2=tumor>3-7 cm in size
T3=tumor>7 cm in size OR multiple tumor nodules in the same lobe
T4=multiple tumor nodules in the same lung but a different lobe The N/M (metastasis) classification is as follows:
N0=no regional lymph node metastasis
N1=metastasis in ipsilateral peribronchial and/or ipsilateral hilar lymph nodes and intrapulmonary nodes, including involvement by direct extension
N2=metastasis in ipsilateral mediastinal and/or subcarinal lymph node(s)
N3=metastasis in contralateral mediastinal, contralateral hilar, ipsilateral or contralateral scalene, or supraclavicular lymph node(s)
M0=no distant metastasis
M1=distant metastasis Tumor stages I to IV are classified in accordance with the above TNM categories as follows:

| Stage | TNM | Description |
|---|---|---|
| Stage I | T1, N0, M0<br>T2a, N0, M0 | T1 = Tumor ≤3 cm in greatest dimension, surrounded by lung or visceral pleura, without bronchoscopic evidence of invasion more proximal than the lobar bronchus (i.e., not in the main bronchus)<br>T2 = Tumor >3 cm but ≤7 cm (T2a: >3 cm but ≤5 cm; T2b: >5 cm but ≤7 cm) in greatest dimension, or tumor with any of the following features: involves main bronchus, ≥2 cm distal to the carina; invades visceral pleura (PL1 or PL2); or is associated with atelectasis or obstructive pneumonitis that extends to the hilar region but does not involve the entire lung.<br>N0 = No regional lymph node metastasis<br>M0 = No distant metastasis |
| Stage II | T1, N1, M0<br>T2b, N0, M0<br>T2, N1, M0<br>T3, N0, M0 | T1, T2, N0, M0: as above<br>T3 = Tumor >7 cm or one that directly invades any of the following: parietal pleural (PL3) chest wall (including superior sulcus tumors), diaphragm, phrenic nerve, mediastinal pleura, or parietal pericardium or tumor in the main bronchus (<2 cm distal to the carina but without involvement of the carina) or associated atelectasis or obstructive pneumonitis of the entire lung or separate tumor nodule(s) in the same lobe<br>N1 = Metastasis in ipsilateral peribronchial and/or ipsilateral hilar lymph nodes and intrapulmonary nodes, including involvement by direct extension |
| Stage III | T1, N2, M0<br>T1, N3, M0<br>T2, N2, M0<br>T2, N3, M0<br>T3, N1, M0<br>T3, N2, M0<br>T3, N3, M0<br>T4, N0, M0<br>T4, N1, M0<br>T4, N2, M0<br>T4, N3, M0 | T1, T2, T3, N1, M0: as above<br>T4 = Tumor of any size that invades any of the following: mediastinum, heart, great vessels, trachea, recurrent laryngeal nerve, esophagus, vertebral body, carina, or separate tumor nodule(s) in a different ipsilateral lobe<br>N2 = Metastasis in ipsilateral mediastinal and/or subcarinal lymph node(s)<br>N3 = Metastasis in contralateral mediastinal, contralateral hilar, ipsilateral or contralateral scalene, or supraclavicular lymph node(s) |

| | | |
|---|---|---|
| Stage IV | Any T, Any N, M1 | T, N: as above<br>M1 = Distant metastasis (Separate tumor nodule(s) in a contralateral lobe tumor with pleural nodules or malignant pleural (or pericardial) effusion and/or distant metastasis in extrathoracic organs) |

Still more detailed information on the staging may be obtained from "Lung" in: Edge S B, Byrd D R, Compton C C, et al., eds.: AJCC Cancer Staging Manual. 7th ed. New York, N.Y.: Springer, 2010, pp 253-70.

The method of the invention pertains to an individual having SCC-NSCLC stage I or II. The diagnosis of SCC-NSCLC stage I or II is within the skills of the competent medical practitioner. As additional means, details on the diagnosis and staging of SCC-NSCLC are given herein.

As detailed herein, a population of individuals having SCC-NSCLC stage I or II can be divided into a high risk group (high risk for relapse) and a low risk group (low risk for relapse) based on the level of the markers Cyfra21-1 and CEA (see FIG. 1 B). As shown in the Examples (e.g. FIG. 2B), only the individuals of the high risk group benefit from chemotherapy.

In order to identify an individual as to be treated by chemotherapy, the amount or concentration of the marker molecules Cyfra21-1 and CEA is measured in a sample obtained from the individual.

Cyfra21-1 belongs to the cytokeratin family. Cytokeratins are structural proteins forming the subunits of epithelial intermediary filaments, which is a major component of the cell cytoskeleton. Twenty different cytokeratin polypeptides with molecule weights ranging from 40 to 70 Kilodaltons (kD) have so far been identified. The type of cytokeratin synthesized by a cell is also affected by the growth and differentiation rate. Due to their specific distribution patterns they are eminently suitable for use as differentiation markers in tumor pathology. CYFRA21-1 is a fragment of cytokeratin 19 which is a part of cytoskeleton in epithelial cells, and can be found in an overexpressed way in tumors of epithelial origin. Intact cytokeratin polypeptides are poorly soluble, but soluble fragments can be detected in serum (Bodenmueller et al., 1994, Int. J. Biol. Markers 9: 75-81). CYFRA21-1 is a well-established marker for Non-Small-Cell Lung Carcinoma (NSCLC). The main indication for CYFRA21-1 is monitoring the course of non-small cell lung cancer (NSCLC) (Sturgeon, 2001, Clinical Chemistry 48: 1151-1159). In primary diagnosis high CYFRA21-1 serum levels indicate an advanced tumor stage and a poor prognosis in patients with non-small-cell lung cancer (van der Gaast et al., 1994, Br. J. Cancer 69: 525-528). A normal or only slightly elevated value does not rule out the presence of a tumor. Successful therapy is documented by a rapid fall in the CYFRA21-1 serum level into the normal range. A constant CYFRA21-1 value or a slight or only slow decrease in the CYFRA21-1 value indicates incomplete removal of a tumor or the presence of multiple tumors with corresponding therapeutic and prognostic consequences.

CEA is a monomeric glycoprotein (molecular weight approx. 180.000 Dalton) with a variable carbohydrate component of approx. 45-60%. CEA, like AFP, belongs to the group of carcinofetal antigens that are produced during the embryonic and fetal period. The CEA gene family consists of about 17 active genes in two subgroups. The first group contains CEA and the Non-specific Cross-reacting Antigens (NCA); the second group contains the Pregnancy-Specific Glycoproteins (PSG). CEA is mainly found in the fetal gastrointestinal tract and in fetal serum. It also occurs in slight quantities in intestinal, pancreatic, and hepatic tissue of healthy adults. The formation of CEA is repressed after birth, and accordingly serum CEA values are hardly measurable in healthy adults. High CEA concentrations are frequently found in cases of colorectal adenocarcinoma (Fateh-Modhadam, A. et al. (eds.), Tumormarker and ihr sinnvoller Einsatz, Juergen Hartmann Verlag GmbH, Marloffstein-Rathsberg (1993), ISBN-3-926725-07-9). Slight to moderate CEA elevations (rarely>10 ng/mL) occur in 20-50% of benign diseases of the intestine, the pancreas, the liver, and the lungs (e.g. liver cirrhosis, chronic hepatitis, pancreatitis, ulcerative colitis, Crohn's Disease, emphysema (Fateh-Moghadam, A., et al., supra). Smokers also have elevated CEA values. The main indication for CEA determinations is therapy management and the follow-up of patients with colorectal carcinoma. CEA determinations are not recommended for cancer-screening in the general population. CEA concentrations within the normal range do not exclude the possible presence of a malignant disease.

In order to identify an individual as to be treated by chemotherapy a sample is obtained from the individual. The individual according to the present invention may be any human or non-human animal, especially a mammal. Thus, the methods and uses described herein are applicable to both human and veterinary disease. Evidently, non-human mammals of particular interest include domestic animals, pets, and animals of commercial value (e.g. domestic animals such as horses) or personal value (e.g. pets such as dogs, cats). The method is especially preferred with human subjects, for which diagnostic methods are commonly employed. In a particularly preferred embodiment the individual is therefore a human.

The sample may be any sample suitable for measuring the markers according to the present invention and refers to a biological sample obtained for the purpose of evaluation in vitro. It comprises material which can be specifically related to the individual and from which specific information about the individual can be determined, calculated or inferred. A sample can be composed in whole or in part of biological material from the patient (e.g., a solid tissue sample obtained from a lung biopsy). A sample can also be material that has contacted the patient in a way that allows tests to be conducted on the sample which provides information about the individual (e.g., broncholavage fluid). The sample may preferably comprise any body fluid. Exemplary test samples include blood, serum, plasma, urine, saliva, and fluid from the lungs (such as epithelial lining fluid), e.g. obtained by bronchoscopy or broncholavage. The sample may be taken from the individual and used immediate or processed before the measuring step a). Processing may include purification (e.g. separation such as centrifugation), concentration, dilution, lysis of cellular components, freezing, acidification, conservation etc. Preferred samples are whole blood, serum, plasma or epithelial lining fluid from the lungs, with plasma, serum or whole blood representing the most convenient type of sample.

Typically, blood-related samples are preferred test samples for use in the context of the present invention. For this, blood may be drawn from a vein, usually from the inside of the elbow or the back of the hand. Particularly, in infants or young children, a sharp tool called a lancet may be used to puncture the skin and make it bleed. The blood may be collected e.g. into a pipette, or onto a slide or test strip. Accordingly, in a preferred embodiment of the present invention, the sample obtained from the individual is a blood sample, particularly selected from the group consisting of serum, plasma, and whole blood.

In a preferred embodiment of the present invention the individual's sample is taken after diagnosis but before therapy. Therapy might have an impact on the marker levels in the individual. Therefore, marker levels representing the state before therapy are rather unaffected and should better reflect the individual's benefit from chemotherapy. The accepted standard treatment of NSCLC stage I and II is surgery, especially surgical resection of the SCC-NSCLC. Typical examples include full lobar or greater resections preferable to sublobar resections. Therefore, the individual's sample may preferably be taken before therapy, particularly before surgery, especially surgical resection of the SCC-NSCLC. The sample may be taken in the range of from 21 days to immediately before therapy, particularly in the range of from 14 days to immediately before for therapy, especially in the range of from 7 days to immediately before therapy. In a preferred embodiment, therapy is surgery; in this case the sample may be taken in the range of from 21 days to immediately before induction of anesthesia for surgery (i.e. before the administration of a drug (combination) at the beginning of an anesthetic that results in a state of general anesthesia), particularly in the range of from 14 days to immediately before induction of anesthesia for surgery, especially in the range of from 7 days to immediately before induction of anesthesia for surgery.

In accordance with the present invention, the amount or concentration of a marker is determined in order to identify a high risk individual to be treated with chemotherapy. The amount of a substance is a standards-defined quantity that measures the size of an ensemble of elementary entities, such as atoms, molecules, electrons, and other particles. It is sometimes referred to as chemical amount. The International System of Units (SI) defines the amount of substance to be proportional to the number of elementary entities present. The SI unit for amount of substance is the mole. It has the unit symbol mol. The concentration of a substance is the amount of a constituent divided by the total volume of a mixture. Several types of mathematical description can be distinguished: mass concentration, molar concentration, number concentration, and volume concentration. The term concentration can be applied to any kind of chemical mixture, but most frequently it refers to solutes and solvents in solutions. The molar (amount) concentration has variants such as normal concentration and osmotic concentration.

A variety of methods for measuring a marker molecule (particularly Cyfra21-1 and CEA) are known in the art and any of these can be used.

Preferably, the marker(s) is/are specifically measured from a liquid sample by use of a specific binding agent.

A specific binding agent is, e.g., a receptor for the marker or an antibody to the marker or a nucleic acid complementary to the nucleic acid relating to the marker protein (e.g. a nucleic acid complementary to a marker's mRNA or relevant part thereof). Preferably, the marker molecule(s) is/are measured at the protein level.

Determination of proteins as binding partners of a marker polypeptide can be performed using any of a number of known methods for identifying and obtaining proteins that specifically interact with proteins or polypeptides, for example, a yeast two-hybrid screening system such as that described in U.S. Pat. Nos. 5,283,173 and 5,468,614, or the equivalent. A specific binding agent has preferably at least an affinity of $10^7$ l/mol for its corresponding target molecule. The specific binding agent preferably has an affinity of $10^8$ l/mol or even more preferred of $10^9$ l/mol for its target molecule. As the skilled artisan will appreciate the term specific is used to indicate that other biomolecules present in the sample do not significantly bind to the binding agent specific for the marker. Preferably, the level of binding to a biomolecule other than the target molecule results in a binding affinity which is only 10% or less, more preferably only 5% or less of the affinity to the target molecule, respectively. A preferred specific binding agent will fulfill both the above minimum criteria for affinity as well as for specificity.

A specific binding agent preferably is an antibody reactive with marker, particularly Cyfra21-1 or CEA. The term antibody refers to a polyclonal antibody, a monoclonal antibody, antigen binding fragments of such antibodies, single chain antibodies as well as to genetic constructs comprising the binding domain of an antibody.

The term "antibodies" includes polyclonal antibodies, monoclonal antibodies, fragments thereof such as F(ab')2, and Fab fragments, as well as any naturally occurring or recombinantly produced binding partners, which are molecules that specifically bind a Cyfra21-1 or CEA polypeptide. Any antibody fragment retaining the above criteria of a specific binding agent can be used. Antibodies are generated by state of the art procedures, e.g., as described in Tijssen (Tijssen, P., Practice and theory of enzyme immunoassays, Elsevier Science Publishers B.V., Amsterdam (1990), the whole book, especially pages 43-78). In addition, the skilled artisan is well aware of methods based on immunosorbents that can be used for the specific isolation of antibodies. By these means the quality of polyclonal antibodies and hence their performance in immunoassays can be enhanced (Tijssen, P., supra, pages 108-115).

For the achievements as disclosed in the present invention polyclonal antibodies raised in e.g. goats may be used. However, clearly also polyclonal antibodies from different species, e.g., rats, rabbits or guinea pigs, as well as monoclonal antibodies can be used. Since monoclonal antibodies can be produced in any amount required with constant properties, they represent ideal tools in development of an assay for clinical routine.

For measurement the sample obtained from an individual is incubated with the specific binding agent for the marker in question under conditions appropriate for formation of a binding agent marker-complex. Such conditions need not be specified, since the skilled artisan without any inventive effort can easily identify such appropriate incubation conditions. The amount of binding agent marker-complex is measured and used in the methods and uses of the invention. As the skilled artisan will appreciate there are numerous methods to measure the amount of the specific binding agent marker-complex all described in detail in relevant textbooks (cf., e.g., Tijssen P., supra, or Diamandis, E. P. and Christopoulos, T. K. (eds.), Immunoassay, Academic Press, Boston (1996)).

Particularly, monoclonal antibodies to the markers (Cyfra21-1 and CEA) is used in quantitative (amount or concentration of the markers is determined) immunoassay.

Preferably, the marker in question is detected in a sandwich type assay format. In such assay a first specific binding agent is used to capture the marker in question on the one side and a second specific binding agent (e.g. a second antibody), which is labeled to be directly or indirectly detectable, is used on the other side. The second specific binding agent may contain a detectable reporter moiety or label such as an enzyme, dye, radionuclide, luminescent group, fluorescent group or biotin, or the like. Any reporter moiety or label could be used with the methods disclosed herein so long as the signal of such is directly related or proportional to the quantity of binding agent remaining on the support after wash. The amount of the second binding agent that remains bound to the solid support is then determined using a method appropriate for the specific detectable reporter moiety or label. For radioactive groups, scintillation counting or autoradiographic methods are generally appropriate. Antibody-enzyme conjugates can be prepared using a variety of coupling techniques (for review see, e.g., Scouten, W. H., Methods in Enzymology 135:30-65, 1987). Spectroscopic methods can be used to detect dyes (including, for example, colorimetric products of enzyme reactions), luminescent groups and fluorescent groups. Biotin can be detected using avidin or streptavidin, coupled to a different reporter group (commonly a radioactive or fluorescent group or an enzyme). Enzyme reporter groups can generally be detected by the addition of substrate (generally for a specific period of time), followed by spectroscopic, spectrophotometric or other analysis of the reaction products. Standards and standard additions can be used to determine the level of antigen in a sample, using well known techniques.

As described above, there are a variety of methods for measuring Cyfra21-1 levels. An assay for "CYFRA21-1" specifically measures a soluble fragment of cytokeratin 19 as present in the circulation. The measurement of CYFRA21-1 is typically based upon two monoclonal antibodies (Bodenmueller et al., 1994, Int. J. Biol. Markers 9: 75-81). Commercially available products for measuring Cyfra21-1 include Enzymum-Test CYFRA 21-1 (Boehringer Mannheim, Mannheim, Germany), Cytokeratin 19 fragment (CYFRA 21-1) immunoradiometric assay kit (Cisbo Assays, Codolet, France), ELISA Kit for Cytokeratin Fragment Antigen 21-1 (Wuhan USCN Business Co., Ltd., China) and the ARCHITECT Cyfra21-1 assay (Abbott, Wiesbaden, Germany). In the CYFRA21-1 assay from Roche Diagnostics, Germany, the two specific monoclonal antibodies (KS 19.1 and BM 19.21) are used and a soluble fragment of cytokeratin 19 having a molecular weight of approx. 30,000 Daltons is measured. Preferably, CYFRA21-1 is measured on an Elecsys® analyzer using Roche product number 11820966160 according to the manufacturer's instructions.

Also for the measurement of CEA levels, there exit a variety of assays. Commercially available products for measuring CEA include the ADVIA Centaur® CEA immunoassay (Siemens Healthcare, Erlangen, Germany) and the ARCHITECT CEA assay (Abbott, Wiesbaden, Germany). Preferably, CEA is measured using "Elecsys® CEA" (Material No: 11731629160, Roche Diagnostics, Ltd, Rotkreuz, Switzerland), which is an electro-chemiluminescence immunoassay (ECLIA) for the quantitative determination of CEA.

The step of measuring the level of a marker may be carried out as follows: The sample and optionally calibrator and/or control may be contacted with the binding agent (which could be immobilized, e.g. on a solid phase) under conditions allowing the binding of the agent to the marker. Unbound binding agents may be removed by a separation step (e.g. one or more washing steps). A second agent (e.g. a labeled agent) may be added to detect the bound binding agent to allow binding to and quantification of the same. Unbound second agent may be removed. The amount of the second binding agent which is proportional to the amount of the marker may be quantified, e.g. based on the label. Quantification may be done based on e.g. a calibration curve constructed for each assay by plotting measured value versus the concentration for each calibrator. The concentration or amount of marker in the sample may be then read from the calibration curve.

After the amount or concentration of the markers is determined (step a), the values for Cyfra21-1 and CEA are combined by weighted calculation of the amount or concentration of the marker molecules measured in step (a) to obtain a combined value (step b) and the value obtained in step (b) is compared to the cut-off value of the combined value as established in a reference population (step c). The expression "comparing the combined value . . . to the cut-off value of the combined value as established in a reference population" is merely used to further illustrate what is obvious to the skilled artisan anyway. In accordance with the present invention, an external control is used as reference population. For the external control the value of the markers in a sample derived from the individual is compared to the respective value obtained in a population of individuals known to have a certain condition (particularly high risk group or low risk group of patients diagnosed with SCC-NSCLC stage I or II). Preferably, the reference group is composed of the patients with SCC-NSCLC stage I or II for which values of Cyfra and CEA before therapy, particularly surgery, are known. The reference population of patients is divided into subgroups, one of which receives chemotherapy and the other does not receive chemotherapy. Benefit from chemotherapy, e.g. relapse free survival, must be known. For example, a marker level (amount or concentration) in a patient sample can be compared to a level known to be associated with a high risk or with a low risk patient. Usually the sample's marker level is directly or indirectly correlated with a diagnosis and the marker level is e.g. used to determine whether an individual should receive chemotherapy. It is within the skills of the practitioner to choose an appropriate control or reference value for the marker established therein. Exemplary populations are given in the Examples. It will be appreciated by the skilled artisan that such control in one embodiment is obtained from a reference population that is age-matched and appropriately categorized into the high and low risk groups of patients with SCC-NSCLC stage I or II. As also clear to the skilled artisan, the absolute marker values established in a control will be dependent on the assay used. Preferably samples from 100 or more well-characterized individuals from the appropriate reference population are used to establish a control (reference) value. Also preferred the reference population may be chosen to consist of at least 20, 30, 50, 100, 200, 500 or 1000 individuals. Preferably, the reference population is diagnosed with SCC-NSCLC stage I or II and does not include individuals diagnosed with non-small cell carcinoma subtype adenocarcinoma.

The values for Cyfra21-1 and CEA as measured in a reference group or a reference population are for example used to establish a median or cut-off value. A value above such median or cut-off value is considered as being indicative for treatment by chemotherapy. In a one embodiment a median or fixed cut-off value is established. Such median or cut-off value is chosen to match the diagnostic question of interest. Preferable, the cut-off is the median of the reference population.

A suitable median or cut-off value may be chosen depending on how many patients one would wish to select for chemotherapy. A higher number of patients selected for chemotherapy decreases the risk to deny a patient chemotherapy who would have benefited from chemotherapy. One the other hand it increases the risk to treat patients who do not benefit from chemotherapy. For a lower number of selected patients the same is true vice versa.

In the present case two markers, namely CEA and Cyfra21-1, are used in the methods of the invention. Accordingly, a combined value is calculated using the amount/concentration of CEA as well as the amount/concentration of Cyfra21-1. The combined value is compared to the combined value of the reference, which has been obtained using the same mathematical procedure. In a preferred embodiment, the combined value is obtained by weighted calculation of the amount or concentration of the marker molecules in the samples. This means that one of the markers is given a higher weighting that the other. The combined value C calculated based on the level (amount or concentration) of CEA ([CEA]) and the level (amount or concentration) of Cyfra21.1 ([Cyfra21.1]) may be obtained e.g. by the following equation:

$$C=a*[CEA]+b*[Cyfra21.1],$$

wherein a and b represent the weighting factors. Preferably, the weighting factors have been obtained by analyzing a reference population. A suitable procedure is described in the Examples.

For example, the combined value of Cyfra21-1 and CEA is determined for each sample of a reference group and subsequent the median or a suitable cut-off of the combined values can be calculated by Cox's proportional hazards regression. In a suitable cohort one may calculate a Cox's proportional hazards regression model with a suitable outcome measurement (e.g. relapse free survival) as a dependent variable and using Cyfra21-1 and CEA as independent variables.

The regression coefficients delivered by the Cox's proportional hazards regression model for Cyfra and CEA can then be used as weighting factors a and b in order to calculate the combined value C for each patient in the cohort. On these combined C values the cut-off can be calculated, e.g. the median of C in the cohort.

Patients with C values above the cut-off would be considered as high risk patients and patients at or below the cut-off as low risk patients. Risk groups may then be compared by Kaplan-Meier curve for illustration purposes.

Cox's proportional hazards regression (Cox, David R 1972 *Journal of the Royal Statistical Society.*, Breslow, N. E. 1975 *International Statistical Review*) is a typical method in survival analysis to examine the relationship of the survival distribution to covariates. The Cox model is usually written in terms of the hazard model formula shown below. This model gives an expression for the hazard at time t for an individual with a given specification of a set of explanatory variables denoted by the X. X presents a collection of predictor variables that is being modeled to predict an individual's hazard. The Cox model formula says that the hazard at time t is the product of two quantities. h0(t) is called the baseline hazard function. The second quantity is the exponential expression e to the linear sum of $\beta_i X_i$, where the sum is over the p explanatory X variables (Gail, M. et al 1996 *Statistics for Biology and Health*).

$$h(t,X)=h0(t)e^{\sum_{i=L}^{p}\beta iXi}$$

Patient categorization may involve Kaplan-Meier (KM) survival curves. A KM curve is a non-parametric statistic used to estimate the survival function from lifetime data (Kaplan, E. L.; Meier, P 1958 J. *Amer. Statist. Assn*). KM curves are not smooth functions, but rather step-wise estimates. The X-axis shows the serial time of the survival duration. The cumulative probability that a member from a given population will have a lifetime exceeding time, t is seen on the Y-axis. Cumulative probabilities for an interval are calculated by multiplying the interval survival rates up to that interval. (Rich J T et al 2010 *Otolaryngol Head Neck Surg*). KM curves were used to show the results of the Examples (see FIGS. 1 to 3). In medical statistics, KM curves are typically applied for grouping patients into categories, for instance, those with Gene A profile and those with Gene B profile. In the graph, patients with Gene B die much more quickly than those with gene A. After two years, about 80% of the Gene A patients survive, but less than half of patients with Gene B. In the present invention, the KM curves are used for grouping patients into high risk and low risk for relapse.

In order to generate a Kaplan-Meier estimator, at least two pieces of data are required for each patient (or each subject): the status at last observation (event occurrence or right-censored) and the time to event (or time to censoring). If the survival functions between two or more groups are to be compared, then a third piece of data is required: the group assignment of each subject. Let S(t) be the probability that a member from a given population will have a lifetime exceeding time, t. For a sample of size N from this population, let the observed times until death of the N sample members be $$t_1 \le t_2 \le t_3 \le \ldots \le t_N.$$

Corresponding to each $t_i$ is $n_i$, the number "at risk" just prior to time $t_i$, and $d_i$ the number of deaths at time $t_i$.

The Kaplan-Meier estimator is the nonparametric maximum likelihood estimate of S(t), where the maximum is taken over the set of all piecewise constant survival curves with breakpoints at the event times $t_i$. It is a product of the form $$\hat{S}(t) = \prod_{t_i < t} \frac{n_i - d_i}{n_i}.$$

When there is no censoring, $n_i$ is just the number of survivors just prior to time $t_i$. With censoring, $n_i$ is the number of survivors minus the number of losses (censored cases). It is only those surviving cases that are still being observed (have not yet been censored) that are "at risk" of an (observed) death. There is an alternative definition that is sometimes used, namely $$\hat{S}(t) = \prod_{t_i \le t} \frac{n_i - d_i}{n_i}.$$

The two definitions differ only at the observed event times. The latter definition is right-continuous whereas the former definition is left-continuous.

Let T be the random variable that measures the time of failure and let F(t) be its cumulative distribution function. Note that $$S(t)=P[T>t]=1-P[T\le t]=1-F(t).$$

Consequently, the right-continuous definition may be preferred in order to make the estimate compatible with a right-continuous estimate of F(t).

The Kaplan-Meier estimator is a statistic, and several estimators are used to approximate its variance. One of the most common such estimators is Greenwood's formula:

$$\widehat{\text{Var}}\left(\hat{S}(t)\right) = \hat{S}(t)^2 \sum_{t_i \leq t} \frac{d_i}{n_i(n_i - d_i)}.$$

In some cases, one may wish to compare different Kaplan-Meier curves. This may be done by several methods including the log rank test or the Cox proportional hazards test.

The above statistical methods are only examples of statistic methods for the identification of high risk patients. The skilled statistician will know suitable methods for analyzing the prevailing data and then providing a suitable cut-off. As detailed above, an individual having a value above the cut-off is identified as high risk.

The individuals identified as being high risk, and therefore to be treated with chemotherapy, have a higher risk for a relapse than the individual classified as low risk. A relapse is a recurrence of a past medical condition, presently the lung adenocarcinoma. The signs and symptoms of the condition return after a remission. Cancer recurrence is defined as the return of cancer after treatment and after a period of time during which the cancer cannot be detected. The same cancer reappears in the same place it was first found or very close by.

The standard therapy with SCC-NSCLC is surgery, especially resection. "Resection" is the surgical removal of part or all of a damaged organ or structure, particularly the removal of a tumor. Lung resection is the surgical removal of all or part of the lung. The type of resection will be based on the tumor location, size, and type, as well as your overall health and lung function prior to diagnosis. On the right side, the lung has three lobes and on the left there are two lobes. Usually, an operation for cancer involves removing a lobe, which is called a lobectomy. Wedge resection or segmentectomy refer to the removal of an area of lung smaller than a lobe, usually the tumor and a small area of healthy lung tissue around it. This is a treatment used for early-stage cancer and sometimes to remove a piece of lung where cancer is suspected but not proven. In a lobectomy, the surgeon removes a lobe of the lungs. This is the usual operation performed for lung cancer, as this has the best chance of removing all the cancerous tissue and decreasing the chance of cancer coming back. Pneumonectomy is the removal of an entire lung. This option is considered if a tumor is especially large, or in a difficult-to-reach or central position in the lung. Although pneumonectomy can result in significant loss of function, many people live quite well with only one lung. Presently, the resections are mainly lobectomies, followed by pneumonectomy, bilobectomy (removal or the right or left lung) and wedge resections.

According to the present invention, high risk patients are to be treated with chemotherapy. "Chemotherapy" is a drug treatment for cancer. It is usually systemic, meaning it circulates through and affects your entire body. The drugs enter the bloodstream and kill abnormal cells or stop them from dividing. They are most often given by intravenous (IV) infusion, into a vein through a catheter, or orally. The cancer's type, stage, and location will determine the specific medicine(s), strength, and frequency of your chemotherapy. It may be combined with surgery or radiation. Chemotherapy may be applied before surgery (sometimes along with radiation therapy) to try to shrink a tumor (neoadjuvant therapy), after surgery (sometimes along with radiation therapy) to try to kill any cancer cells that may have been left behind (adjuvant therapy) or as the main treatment (sometimes along with radiation therapy) for more advanced cancers or for some people who aren't healthy enough for surgery. It is usually given in cycles, with a period of treatment (usually 1 to 3 days) followed by a rest period to allow the body time to recover. Some chemotherapeutics, though, are given every day. Cycles generally last about 3 to 4 weeks. Examples of chemotherapeutics include cisplatin, carboplatin, paclitaxel (Taxol®), albumin-bound paclitaxel (nab-paclitaxel, Abraxane®), docetaxel (Taxotere®), gemcitabine (Gemzar®), vinorelbine (Navelbine®), irinotecan (Camptosar®), etoposide (VP-16®), vinblastine or pemetrexed (Alimta®). Most often, treatment for NSCLC uses a combination of 2 chemotherapeutics. Studies have shown that adding a third drug does not add much benefit and is likely to cause more side effects. Single-drug chemo is sometimes used for people who might not tolerate combination chemotherapy well, such as those in poor overall health or who are elderly. If a combination is used, it often includes cisplatin or carboplatin plus one other drug. Sometimes combinations that do not include these drugs, such as gemcitabine with vinorelbine or paclitaxel, may be used. Individuals with advanced lung cancers who meet certain criteria, a targeted therapy drug such as bevacizumab (Avastin®) or cetuximab (Erbitux®) may be added to treatment as well. Presently preferred adjuvant chemotherapies include cisplatin or carboplatin, often in combination vinorelbine, docetaxel, etoposid or permetrexed. In the present invention, the chemotherapy is preferably adjuvant chemotherapy. More preferably, the individual is to be treated with chemotherapy after surgery, especially after surgical resection of the SCC-NSCLC.

A further treatment of lung cancer is radiotherapy. Radiotherapy is often given together with chemotherapy, and may be used with curative intent in people with NSCLC who are not eligible for surgery. This form of high-intensity radiotherapy is called radical radiotherapy. A refinement of this technique is continuous hyperfractionated accelerated radiotherapy (CHART), in which a high dose of radiotherapy is given in a short time period. Postoperative thoracic radiotherapy generally should not be used after curative intent surgery for NSCLC. If cancer growth blocks a short section of bronchus, brachytherapy (localized radiotherapy) may be given directly inside the airway to open the passage. Compared to external beam radiotherapy, brachytherapy allows a reduction in treatment time and reduced radiation exposure to healthcare staff. Evidence for brachytherapy, however, is less than that for external beam radiotherapy. In the present invention, chemotherapy, particularly adjuvant chemotherapy may be combined with radiotherapy.

In a second aspect, the present invention relates to the use of CYFRA 21-1 and CEA as marker combination for the identification of an individual to be treated by chemotherapy, wherein the detection of a combined value of the marker combination in a sample obtained from an individual above the cut-off value of the combined values as established in a reference population or reference group is indicative of the treatment by chemotherapy, wherein the combined value is obtained by weighted calculation of the amount or concentration of the marker molecules in the samples and wherein the individual is diagnosed with SCC-NSCLC stage I or II.

The use according to the invention may be further defined as specified for the method of the present invention. Particularly, with respect to the terms used in the second aspect of the present disclosure it is referred to the terms, examples and specific embodiments used in the first aspect of the present disclosure, which are also applicable to the second aspect of the present disclosure.

In general, the disclosure is not limited to the particular methodology, protocols, and reagents described herein because they may vary. Further, the terminology used herein is for the purpose of describing particular embodiments only and is not intended to limit the scope of the present disclosure. As used herein and in the appended claims, the singular forms "a", "an", and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the disclosure. Although any methods and materials similar or equivalent to those described herein can be used in the practice as presented herein, the specific methods, and materials are described herein.

The disclosure is further illustrated by the following examples, although it will be understood that the examples are included merely for purposes of illustration and are not intended to limit the scope of the disclosure unless otherwise specifically indicated.

EXAMPLES

Example 1

Definition of Weighting Factors and Cut-Off Value in a Reference Population

Example 1 describes how the weighting factors for the combination of Cyfra21-1 and CEA and the cut-off value on the combined value C are obtained in suitable reference population.

A suitable reference population should consist of patients with SCC-NSCLC for which baseline (before surgery) levels of Cyfra21-1 and CEA are known, a part of the patients should have received chemotherapy and a suitable outcome measurement (e.g. relapse free survival) should be available.

In a suitable cohort one may calculate a Cox's proportional hazards regression model with a suitable outcome measurement (e.g. relapse free survival) as a dependent variable and using Cyfra21-1 and CEA and optionally T-stage as independent variables.

The regression coefficients delivered by the Cox's proportional hazards regression model for Cyfra21-1, CEA and optionally T-stage can then be used as weighting factors in order to calculate the combined value C for each patient in the cohort. On these combined C values the cut-off can be defined, e.g. by calculation of the median of the C values in the cohort.

Patients with C values above the cut-off would be considered as high risk patients and patients at or below the cut-off as low risk patients. If the weighting factors for calculation of the combined value and the cut-off are established these results then can be used for the selection of new patients for chemotherapy.

Example 2

Determining Effectiveness of Chemotherapy in Various Subgroups of Patients with Stage I and II SCC-NSCLC A population of 88 patients with stage I and II SCC-NSCLC was used in order to identify subgroups of patients, depending on their tumor stage and marker levels. It was the aim to clarify whether or not all subgroups should be treated by chemotherapy.

All patients underwent a resection of the tumor whereas 21 of these patients received chemotherapy in addition. The concentration of Cyfra21-1 and CEA were measured in serum samples which were collected before the resection.

The criterion which today is mostly used in clinical practice to select patients for chemotherapy is based on tumor size. To evaluate the suitability of stage to select patients for chemotherapy in the present cohort patients with stage T1-2,N0 were considered as low risk and patients with stage T3,N0 or T1-2,N1 were considered as high risk. Differences in relapse-free survival for patients with or without chemotherapy in the high and low risk group according to stage were assessed (Table 1).

TABLE 1

Risk groups based on stage.

| | With Chemotherapy | | Without Chemotherapy | | |
|---|---|---|---|---|---|
| | Survival (RFS) | Variance | Survival (RFS) | Variance | p value |
| Low risk group | | | | | |
| 1 year | 1 | 0.0833 | 0.86 | 0.0036 | 0.6399 |
| 2 years | 1 | 0.0833 | 0.7 | 0.0087 | 0.3096 |
| 3 years | 1 | 0.0833 | 0.65 | 0.0115 | 0.2374 |
| High risk group | | | | | |
| 1 year | 0.88 | 0.0078 | 0.69 | 0.0375 | 0.2069 |
| 2 years | 0.88 | 0.0133 | 0.62 | 0.0375 | 0.1038 |
| 3 years | 0.82 | 0.0133 | 0.56 | 0.0514 | 0.09404 |

HR low risk group: chemo vs. no chemo = 2.373 (p = 0.3905)
HR high risk group: chemo vs. no chemo = 2.161 (p = 0.2211)

For the evaluation of the suitability of Cyfra21-1 and CEA to select patients for chemotherapy a Cox's proportional hazards regression model was then established on the present population with relapse free survival as a dependent variable and Cyfra21-1 and CEA as independent variables.

The combined value C for each patient was then calculated by:

$$C = b_1 * \log 2(\text{Cyfra21-1}) + b_2 * \log 2(\text{CEA})$$

wherein $b_1$, $b_2$ are the regression coefficients derived from the Cox's proportional hazards regression model and log 2( . . . ) represents the logarithm to base 2. In the described cohort $b_1$ was 0.459 and $b_2$ was 0.017.

Thus to each patient in the population a combined value C was assigned. The median of these C values was then defined as a cut-off (in described cohort the median was 0.960). All patients with a combined value C above the cut-off were considered as high risk patients and patients at or below the cut-off as low risk patients.

It was observed that patients in the high risk group who received chemotherapy had had a significantly longer relapse free survival as compared to patients in the high risk group which did not receive chemotherapy. In the low risk group however there was no significant difference in relapse free survival between patients with or without chemotherapy observable. This implies that all patients in the high risk group should receive chemotherapy whereas patients from the low risk group should not receive chemotherapy.

Differences in relapse free survival between patients with or without chemotherapy in the high or respectively the low risk group were estimated by the hazard ratio and by the proportion of relapse free survival after 1, 2 and 3 years.

The hazard ratio was calculated by a second Cox's proportional hazards regression model with the binary factor chemotherapy yes/no as an independent variable and relapse free survival as dependent variable. The Cox's proportional hazards regression model was separately calculated in the high risk group and the low risk group. Results are shown in table 2.

TABLE 2

Risk groups based on Cyfra21-1 and CEA.

|  | With Chemotherapy | | Without Chemotherapy | | |
| --- | --- | --- | --- | --- | --- |
|  | Survival (RFS) | Variance | Survival (RFS) | Variance | p value |
| Low risk group | | | | | |
| 1 year | 0.92 | 0.0076 | 0.88 | 0.0045 | 0.6736 |
| 2 years | 0.92 | 0.0076 | 0.84 | 0.0059 | 0.4707 |
| 3 years | 0.92 | 0.0076 | 0.84 | 0.0059 | 0.4707 |
| High risk group | | | | | |
| 1 year | 0.89 | 0.0317 | 0.77 | 0.0099 | 0.5045 |
| 2 years | 0.89 | 0.0317 | 0.54 | 0.0255 | 0.0497 |
| 3 years | 0.78 | 0.0317 | 0.43 | 0.0408 | 0.0351 |

HR low risk group: chemo vs. no chemo = 0.876 (p = 0.8468)
HR high risk group: chemo vs. no chemo = 3.984 (p = 0.0627).

Example 3

Identifying a Patient as to be Treated by Chemotherapy

For a new patient one measures Cyfra21-1 and CEA from a suitable sample from this patient and calculates based on the defined weighting factors the combined value C of this patient. If for the patient the combined value C is above the previously defined cut-off one would select this patient for chemotherapy.

The weighting factors and the cut-off for the combined value C can be derived from any suitable cohort as described in Example 1 if one desires to independently establish such weighting factors and such cut-off value or one can use the weighting factors and the cut-off value as given in Example 2.

The invention claimed is:

1. A method of identifying that a human individual diagnosed as having non-small cell lung carcinoma subtype squamous cell carcinoma (SCC-NSCLC) stage I or II is to be treated by chemotherapy following resection of the SCC-NSCLC, the method comprising
    a) obtaining a sample from the human individual diagnosed as having SCC-NSCLC stage I or II;
    b) measuring the amount or concentration of the cytokeratin-19 fragments (CYFRA 21-1) protein and carcinoembryonic antigen (CEA) protein in the sample using a specific binding agent for CYFRA 21-1 and a specific binding agent for CEA;
    c) obtaining a combined value by weighted calculation of the amount or concentration of the CYFRA 21-1 protein and the CEA protein measured in step (b); and
    d) comparing the combined value for the CYFRA 21-1 protein and the CEA protein obtained in step (c) to a cut-off value of the combined values as established in a reference population diagnosed with SCC-NSCLC stage I or II;
    e) identifying that the human individual is to be treated by chemotherapy following resection of the SCC-NSCLC when an increased combined value is detected as compared to the combined values of the reference population; and
    f) treating the identified human individual with a chemotherapy.

2. The method of claim 1, wherein the human individual's sample is obtained before surgical resection of the SCC-NSCLC.

3. The method of claim 2, wherein the individual's sample is obtained in the range of from 21 days to immediately before surgical resection.

4. The method of claim 1, wherein the reference population is diagnosed with SCC-NSCLC stage I or II and does not include individuals diagnosed with non-small cell lung carcinoma subtype adenocarcinoma.

5. The method of claim 1, wherein the sample is serum, plasma, or whole blood.

6. The method of claim 1, wherein the cut-off value is the median of the reference population.

7. The method of claim 1, wherein the chemotherapy is selected from the group consisting of cisplatin, carboplatin, paclitaxel, albumin-bound paclitaxel, docetaxel, gemcitabine, vinorelbine, irinotecan, etoposide, vinblastine, pemetrexed, and combinations thereof.

8. The method of claim 1, wherein the specific binding agent for CYFRA 21-1 is an antibody specifically binding CYFRA 21-1 and a specific binding agent for CEA is an antibody specifically binding CEA.

* * * * *